(12) United States Patent
Holm et al.

(10) Patent No.: US 10,537,478 B2
(45) Date of Patent: Jan. 21, 2020

(54) NEGATIVE PRESSURE WOUND DRESSING WITH ABSORBENT ADHESIVE SEALANT LAYER

(71) Applicant: 3M INNOVATIVE PROPERTIES COMPANY, Saint Paul, MN (US)

(72) Inventors: David R. Holm, Hudson, WI (US); James M. Sieracki, Brooklyn Center, MN (US); Simon S. Fung, Woodbury, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 341 days.

(21) Appl. No.: 15/539,855

(22) PCT Filed: Dec. 28, 2015

(86) PCT No.: PCT/US2015/067661
§ 371 (c)(1),
(2) Date: Jun. 26, 2017

(87) PCT Pub. No.: WO2016/109420
PCT Pub. Date: Jul. 7, 2016

(65) Prior Publication Data
US 2017/0367895 A1 Dec. 28, 2017

Related U.S. Application Data

(60) Provisional application No. 62/112,714, filed on Feb. 6, 2015, provisional application No. 62/098,058, filed on Dec. 30, 2014.

(51) Int. Cl.
*A61F 13/02* (2006.01)
*A61L 15/42* (2006.01)
(Continued)

(52) U.S. Cl.
CPC .... *A61F 13/0253* (2013.01); *A61F 13/00063* (2013.01); *A61F 13/0206* (2013.01);
(Continued)

(58) Field of Classification Search
CPC ............ A61F 13/0253; A61F 13/00063; A61F 13/0206; A61F 13/0216; A61F 13/0266;
(Continued)

(56) References Cited

U.S. PATENT DOCUMENTS

RE24,906 E 12/1960 Ulrich
3,389,827 A 6/1968 Abere
(Continued)

FOREIGN PATENT DOCUMENTS

EP 2437803 4/2012
EP 2440260 4/2012
(Continued)

OTHER PUBLICATIONS

International Search Report for PCT International Application No. PCT/US2015/067661, dated Apr. 22, 2016, 5 pages.

*Primary Examiner* — Philip R Wiest
(74) *Attorney, Agent, or Firm* — 3M Innovative Properties Company; Trisha D. Adamson

(57) ABSTRACT

A wound dressing is provided. The dressing includes a moisture-transmissible backing layer having a first major surface, a second major surface, a backing layer perimeter, and a first opening; an absorbent adhesive gel adhered to the second major surface of the backing layer, the absorbent adhesive gel comprising an adhesive gel perimeter; and a porous layer having a first side, a second side, and a porous layer perimeter. The second major surface has a first adhesive disposed thereon. The first side of the porous layer is adhered to the absorbent adhesive gel. The porous layer is configured to facilitate passage of fluid to the first opening.

(Continued)

One-hundred percent of the adhesive gel perimeter is overlapped by the backing layer. At least 50% of the porous layer perimeter is overlapped by the absorbent adhesive gel.

20 Claims, 5 Drawing Sheets

(51) Int. Cl.
<table>
<tr><td>A61L 15/60</td><td>(2006.01)</td></tr>
<tr><td>B32B 3/00</td><td>(2006.01)</td></tr>
<tr><td>A61L 15/46</td><td>(2006.01)</td></tr>
<tr><td>A61F 13/00</td><td>(2006.01)</td></tr>
<tr><td>A61L 15/22</td><td>(2006.01)</td></tr>
<tr><td>A61L 15/44</td><td>(2006.01)</td></tr>
<tr><td>A61L 15/58</td><td>(2006.01)</td></tr>
<tr><td>A61L 15/24</td><td>(2006.01)</td></tr>
<tr><td>A61L 15/26</td><td>(2006.01)</td></tr>
</table>

(52) U.S. Cl.
CPC ...... *A61F 13/0216* (2013.01); *A61F 13/0266* (2013.01); *A61L 15/22* (2013.01); *A61L 15/24* (2013.01); *A61L 15/26* (2013.01); *A61L 15/425* (2013.01); *A61L 15/44* (2013.01); *A61L 15/46* (2013.01); *A61L 15/58* (2013.01); *A61L 15/60* (2013.01); *B32B 3/00* (2013.01); *A61L 2300/404* (2013.01)

(58) Field of Classification Search
CPC .......... A61L 15/22; A61L 15/24; A61L 15/26; A61L 15/425; A61L 15/44; A61L 15/46; A61L 15/58; A61L 15/60
See application file for complete search history.

(56) References Cited

U.S. PATENT DOCUMENTS

<table>
<tr><td>3,645,835</td><td>A</td><td>2/1972</td><td>Hodgson</td></tr>
<tr><td>4,112,213</td><td>A</td><td>9/1978</td><td>Waldman</td></tr>
<tr><td>4,310,509</td><td>A</td><td>1/1982</td><td>Berglund</td></tr>
<tr><td>4,323,557</td><td>A</td><td>4/1982</td><td>Rosso</td></tr>
<tr><td>4,595,001</td><td>A</td><td>6/1986</td><td>Potter</td></tr>
<tr><td>4,737,410</td><td>A</td><td>4/1988</td><td>Kantner</td></tr>
<tr><td>4,931,282</td><td>A</td><td>6/1990</td><td>Asmus</td></tr>
<tr><td>4,969,880</td><td>A</td><td>11/1990</td><td>Zamierowski</td></tr>
<tr><td>5,088,483</td><td>A</td><td>2/1992</td><td>Heinecke</td></tr>
<tr><td>5,160,315</td><td>A</td><td>11/1992</td><td>Heinecke</td></tr>
<tr><td>5,225,473</td><td>A</td><td>7/1993</td><td>Duan</td></tr>
<tr><td>5,261,893</td><td>A</td><td>11/1993</td><td>Zamierowski</td></tr>
<tr><td>5,389,376</td><td>A</td><td>2/1995</td><td>Duan</td></tr>
<tr><td>5,409,966</td><td>A</td><td>4/1995</td><td>Duan</td></tr>
<tr><td>5,527,293</td><td>A</td><td>6/1996</td><td>Zamierowski</td></tr>
<tr><td>6,071,267</td><td>A</td><td>6/2000</td><td>Zamierowski</td></tr>
<tr><td>6,171,985</td><td>B1</td><td>1/2001</td><td>Joseph</td></tr>
<tr><td>6,242,665</td><td>B1</td><td>6/2001</td><td>Malowaniec</td></tr>
<tr><td>6,368,687</td><td>B1</td><td>4/2002</td><td>Joseph</td></tr>
<tr><td>6,461,467</td><td>B2</td><td>10/2002</td><td>Blatchford</td></tr>
<tr><td>6,479,724</td><td>B1</td><td>11/2002</td><td>Areskoug</td></tr>
<tr><td>D468,548</td><td>S</td><td>1/2003</td><td>Head, Jr.</td></tr>
<tr><td>7,520,872</td><td>B2</td><td>4/2009</td><td>Biggie</td></tr>
<tr><td>7,731,702</td><td>B2</td><td>6/2010</td><td>Bybordi</td></tr>
<tr><td>8,546,637</td><td>B2</td><td>10/2013</td><td>Holm</td></tr>
<tr><td>8,556,871</td><td>B2</td><td>10/2013</td><td>Mormino</td></tr>
<tr><td>9,278,155</td><td>B2</td><td>3/2016</td><td>Asmus</td></tr>
<tr><td>1,013,052</td><td>A1</td><td>11/2018</td><td>Junginger</td></tr>
<tr><td>1,032,400</td><td>A1</td><td>6/2019</td><td>Thompson</td></tr>
<tr><td>2004/0247655</td><td>A1</td><td>12/2004</td><td>Asmus</td></tr>
<tr><td>2008/0233348</td><td>A1</td><td>9/2008</td><td>Ishiwatari</td></tr>
<tr><td>2009/0187130</td><td>A1</td><td>7/2009</td><td>Asmus</td></tr>
<tr><td>2009/0216168</td><td>A1</td><td>8/2009</td><td>Eckstein</td></tr>
<tr><td>2009/0299251</td><td>A1</td><td>12/2009</td><td>Buan</td></tr>
<tr><td>2010/0159192</td><td>A1</td><td>6/2010</td><td>Cotton</td></tr>
<tr><td>2012/0095380</td><td>A1</td><td>4/2012</td><td>Gergely</td></tr>
<tr><td>2012/0209226</td><td>A1</td><td>8/2012</td><td>Simmons</td></tr>
<tr><td>2014/0024989</td><td>A1</td><td>1/2014</td><td>Ueda</td></tr>
<tr><td>2014/0124232</td><td>A1</td><td>5/2014</td><td>Sarchi</td></tr>
<tr><td>2014/0249495</td><td>A1</td><td>9/2014</td><td>Mumby</td></tr>
<tr><td>2014/0350494</td><td>A1*</td><td>11/2014</td><td>Hartwell ............. A61F 13/0216<br>604/319</td></tr>
<tr><td>2016/0120706</td><td>A1*</td><td>5/2016</td><td>Collinson ........... A61F 13/0253<br>604/319</td></tr>
<tr><td>2017/0143552</td><td>A1</td><td>5/2017</td><td>Hartwell</td></tr>
</table>

FOREIGN PATENT DOCUMENTS

<table>
<tr><td>GB</td><td>2496310</td><td>5/2013</td></tr>
<tr><td>WO</td><td>WO 1999-27975</td><td>6/1999</td></tr>
<tr><td>WO</td><td>WO 2003-086493</td><td>10/2003</td></tr>
<tr><td>WO</td><td>WO 2004-108854</td><td>12/2004</td></tr>
<tr><td>WO</td><td>WO 2009-091682</td><td>7/2009</td></tr>
<tr><td>WO</td><td>WO 2010-056541</td><td>5/2010</td></tr>
<tr><td>WO</td><td>WO 2010-056543</td><td>5/2010</td></tr>
<tr><td>WO</td><td>WO 2011-135284</td><td>11/2011</td></tr>
<tr><td>WO</td><td>WO 2012-156655</td><td>11/2012</td></tr>
<tr><td>WO</td><td>WO 2014-003957</td><td>1/2014</td></tr>
<tr><td>WO</td><td>WO 2014-020440</td><td>2/2014</td></tr>
<tr><td>WO</td><td>WO 2014-140608</td><td>9/2014</td></tr>
<tr><td>WO</td><td>WO 2015-134249</td><td>9/2015</td></tr>
<tr><td>WO</td><td>WO 2016-109418</td><td>7/2016</td></tr>
</table>

* cited by examiner

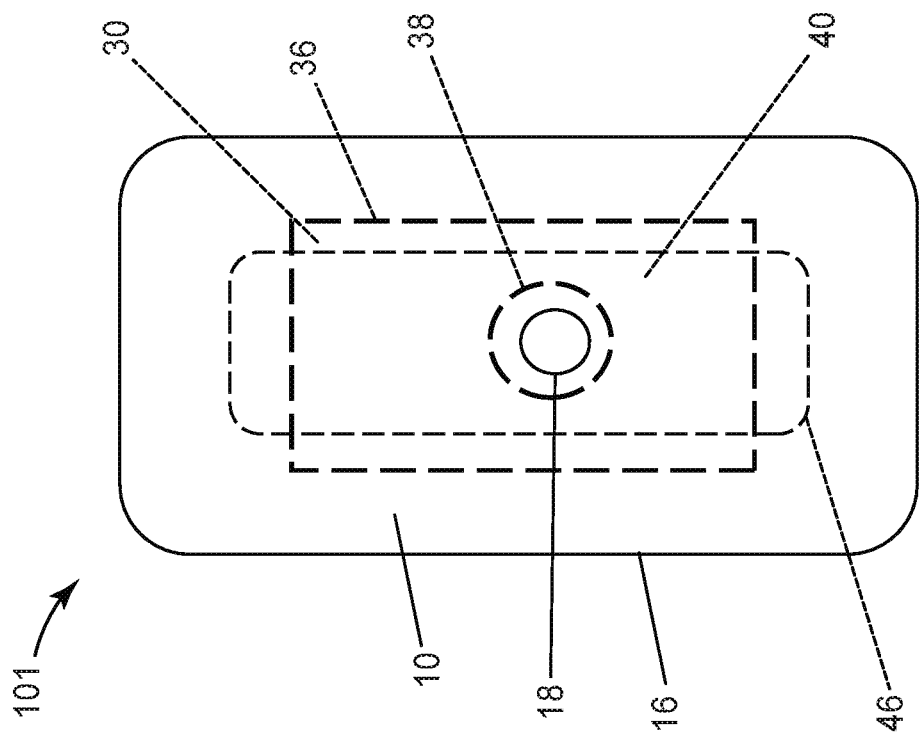
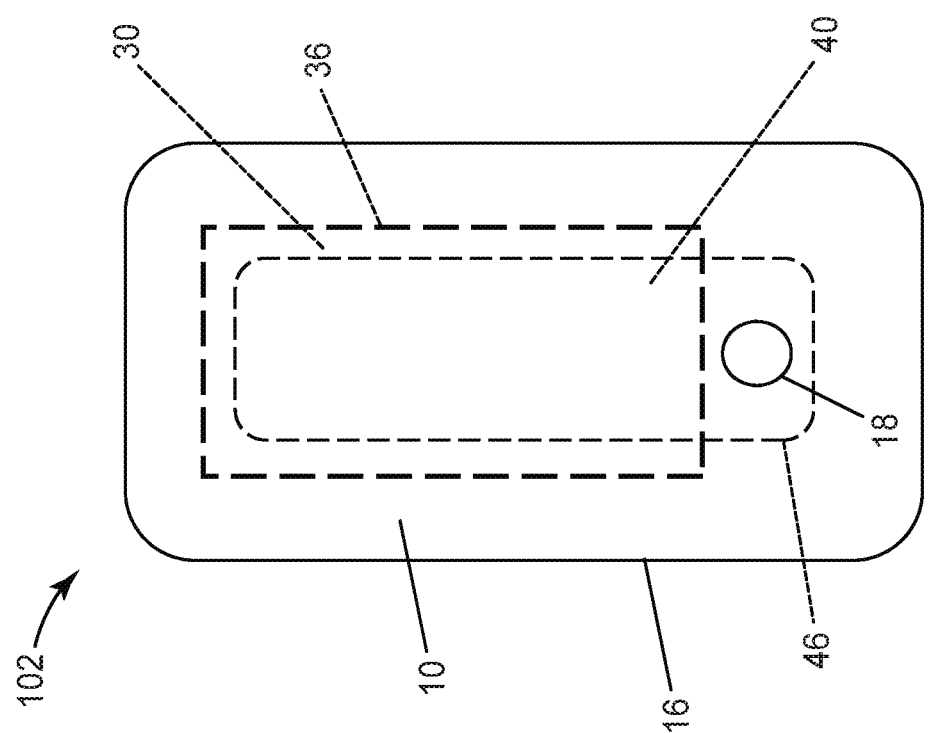

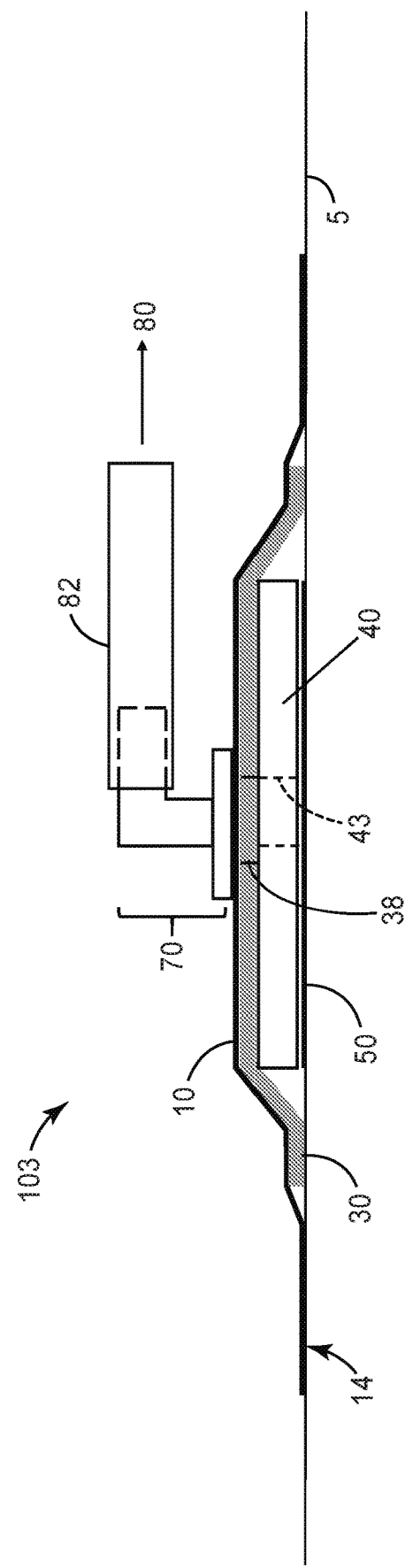

NEGATIVE PRESSURE WOUND DRESSING WITH ABSORBENT ADHESIVE SEALANT LAYER

CROSS REFERENCE TO RELATED APPLICATIONS

This application is a national stage filing under 35 U.S.C. 371 of PCT/US2015/067661, filed Dec. 28, 2015, which claims the benefit of both U.S. Provisional Application No. 62/112,714, filed Feb. 6, 2015, and U.S. Provisional Application No. 62/098,058, filed Dec. 30, 2014, the disclosures of which are incorporated by reference in their entirety herein.

BACKGROUND

The treatment of wounds has resulted in the development of a variety of methods to facilitate healing. One popular technique has been to use negative pressure therapy ("NPT"), which is also known as suction or vacuum therapy. Various NPT devices have been developed to allow exudates (i.e., body secretions) to be removed while at the same time isolating the wound to protect it so that its recovery time is reduced.

A more recently developed form of NPT is known as vacuum assisted closure ("VAC") techniques. The use of VAC techniques in the treatment of wounds is based on the premise that, when controlled negative pressure is applied to a wound, it stimulates mitosis, which leads to formation of new vessels and wound closure.

Studies have shown that this treatment assists wound healing by providing a moist protective environment, by reducing peripheral edema around the wound, by stimulating circulation to the wound bed, by decreasing bacterial colonization, and by increasing the rate of granulation tissue formation and epithelialization.

NPT is useful in the treatment of a variety of wound types, including acute, subacute, chronic, traumatic, graphs, flaps, pressure ulcers, and diabetic ulcers. NPT also has been shown to facilitate healing in deep wounds or cavity wounds. In particular, it allows the dead tissue, debris, and/or exudates to be drawn from the wound area under vacuum pressure which increases the rate of healing. In addition, the use of NPT on surgically closed incision has been shown to reduce complications, increase tissue-tissue apposition, and reduce scarring.

These methods typically include a watertight seal over the wound. Generally, the watertight seal is adhered to the portion of the outer skin which surrounds the wound area. One type of wound dressing inserts a porous foam into the wound. Sometimes, a drainage tube, a drainage pump, and a dressing cover are combined with the porous foam insert to form a system which siphons exudates from the wound. There are problems associated with this type of dressing. Another type of dressing has been developed which uses a flexible single piece dressing that has a unitary structure which combines a drainage tube as an integral part of the outer wound cover.

In spite of the variety of available wound dressings, including NPT wound dressings, there remains a need for a wound dressing that can manage wound exudate and provide an environment that facilitates tissue healing.

SUMMARY

The present disclosure generally relates to wound dressings. In particular, the present disclosure relates to wound dressings that can be connected to a source of negative pressure in order to remove undesirable and/or excess fluid at a wound site and thereby promote tissue healing. The wound dressing of the present disclosure advantageously provides two routes for the movement of liquid away from the wound site: 1) a manifold porous layer placed in conjunction with a liquid path leading to a vacuum source and 2) a highly moisture-transmissible laminate comprising an absorbent adhesive gel and a backing layer that provide a means for evaporative moisture loss through the wound dressing. In addition, the highly-conformable absorbent adhesive gel facilitates sealing of the dressing to the skin and thereby helps maintain negative pressure to the wound site even when the dressing is applied to relatively mobile anatomical sites such as a joint (e.g., a knee joint), for example. The gels function as absorbent reservoirs for excess wound exudate with high retention of moisture relative to other absorbent layers in the dressing, which enables the use of a smaller canister (i.e., collection reservoir) when the dressing is for negative pressure wound therapy. Finally, the absorbent adhesive gel provides gentle adhesion to dry periwound skin which reduces skin trauma upon removal and it also provides added securement of the wound site from undesirable shear forces.

In one aspect, the present disclosure provides a wound dressing. The wound dressing can comprise a moisture-transmissible backing layer having a first major surface, a second major surface, a backing layer perimeter, and a first opening; an absorbent adhesive gel adhered to at least a portion of the second major surface of the backing layer, the absorbent adhesive gel comprising an adhesive gel perimeter; and a porous layer having a first side, a second side, and a porous layer perimeter. The second major surface has a first adhesive disposed thereon proximate the backing layer perimeter. The first side of the porous layer is adhered to the absorbent adhesive gel. The porous layer is configured to facilitate passage of fluid to the first opening. One-hundred percent of the adhesive gel perimeter is overlapped by the backing layer. At least 50% of the porous layer perimeter is overlapped by the absorbent adhesive gel.

Optionally, in any embodiment, the absorbent adhesive gel has a second opening. In these embodiments, at least a portion of the first opening overlaps at least a portion of the second opening.

In any embodiment, at least 50% of the porous layer perimeter is overlapped by the absorbent adhesive gel. In any embodiment, more than 50% of the porous layer perimeter is overlapped by the absorbent adhesive gel.

In any of the above embodiments, the absorbent adhesive gel can have a thickness of about 0.2 mm to about 4.0 mm. In any of the above embodiments, the absorbent adhesive gel can comprise less than 40% (w/w) water. In any of the above embodiments, the dressing further comprises perforated layer adhered to the second side of the porous layer. In any of the above embodiments; the perforated layer, when present, can have a first major surface facing the second side of the porous layer and a second major surface opposite the first major surface, wherein the second major surface includes a silicone adhesive. In any of the above embodiments, the backing layer with the absorbent adhesive gel adhered thereto can have a Moisture Vapor Transmission Rate $\geq 1$ g/10 cm$^2$/24 hours, as measured by EN-13726-1: 2002 Section 3.3. In any of the above embodiments, the absorbent adhesive gel can have a shear modulus, G', between about 0.5 newtons/cm$^2$ and about 5 newtons/cm$^2$ at 24° C. at a shear of 1 rad/sec. In any of the above embodiments, the absorbent adhesive gel can have a loss shear modulus, G" between about 0.2 newtons/cm$^2$ and about 2 newtons/cm$^2$ at 24° C. at a shear of 1 rad/sec. In any of the above embodiments, the porous absorbent layer can comprise open-cell foam (preferably, a non-water-swellable foam such as the foam used in GRANUFOAM™ dressings available from Kinetic Concepts, Inc. (San Antonio, Tex.) or the foam used in 3M™ TEGADERM™ High Performance Foam Adhesive Dressings available from 3M Company (St. Paul, Minn.)), a woven fabric, or a nonwoven fabric. In any of the above embodiments, the absorbent adhesive gel is capable of absorbing ≥1.5 times its dry weight when contacted with an isotonic saline solution at 37° C. for 24 hours.

As used herein "hydrogel," and "hydrophilic gel" refers to a continuous phase of a hydrophilic polymer that is capable of swelling on contact with water and other hydrophilic swelling agents. The term is used regardless of the state of hydration. Useful hydrogels will absorb at least 40% by weight based on the hydrogel's weight in an anhydrous state. Hydrogels are hydrophilic polymers characterized by their hydrophilicity (i.e., capable of absorbing large amounts of fluid such as wound exudate). The hydrogels are typically transparent or translucent, regardless of their degree of hydration. Hydrogels are generally distinguishable from hydrocolloids, which typically comprise a hydrophobic matrix that contains dispersed hydrophilic particles.

As used herein, "hydrocolloid" refers to a continuous phase of hydrophobic polymer containing 15-45% by weight of absorbent hydrophilic particles, polymers, or fibers dispersed therein. The hydrophobic polymer can be based on silicone or polyolefin. Useful hydrocolloids (when used as the absorbent adhesive gel) will absorb at least 150% by weight based on its dry weight.

The terms "comprises" and variations thereof do not have a limiting meaning where these terms appear in the description and claims.

As used herein, "a," "an," "the," "at least one," and "one or more" are used interchangeably. Thus, for example, a porous layer can be interpreted to mean "one or more" porous layers.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF DRAWINGS

FIGS. 3A and 3B are schematic plan views of an alternative embodiments of a wound dressing according to the present disclosure, wherein the absorbent adhesive gel perimeter does not overlap 100% of the porous layer perimeter.

FIG. 4 is a schematic side view of one embodiment of a wound dressing of the present disclosure applied to a treatment site, the wound dressing comprising a vacuum port.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the device, to indicate or imply necessary or required orientations of the device, or to specify how the invention described herein will be used, mounted, displayed, or positioned in use.

The present disclosure generally relates to negative pressure-type wound dressings. These dressings are used to manage fluid accumulation at a wound site and to create an interfacial pressure between the wound surface and the wound covering such that the formation and growth of granulation tissue is stimulated. The inventive dressing provides two distinct mechanisms (e.g., egress routes) for fluid management. In addition, the materials from which the dressing is constructed provide a surface that facilitates conformity of the wound to anatomical structure and that maintains a negative pressure environment for extended periods of time, relative to other negative pressure dressing configurations.

Figure 1:
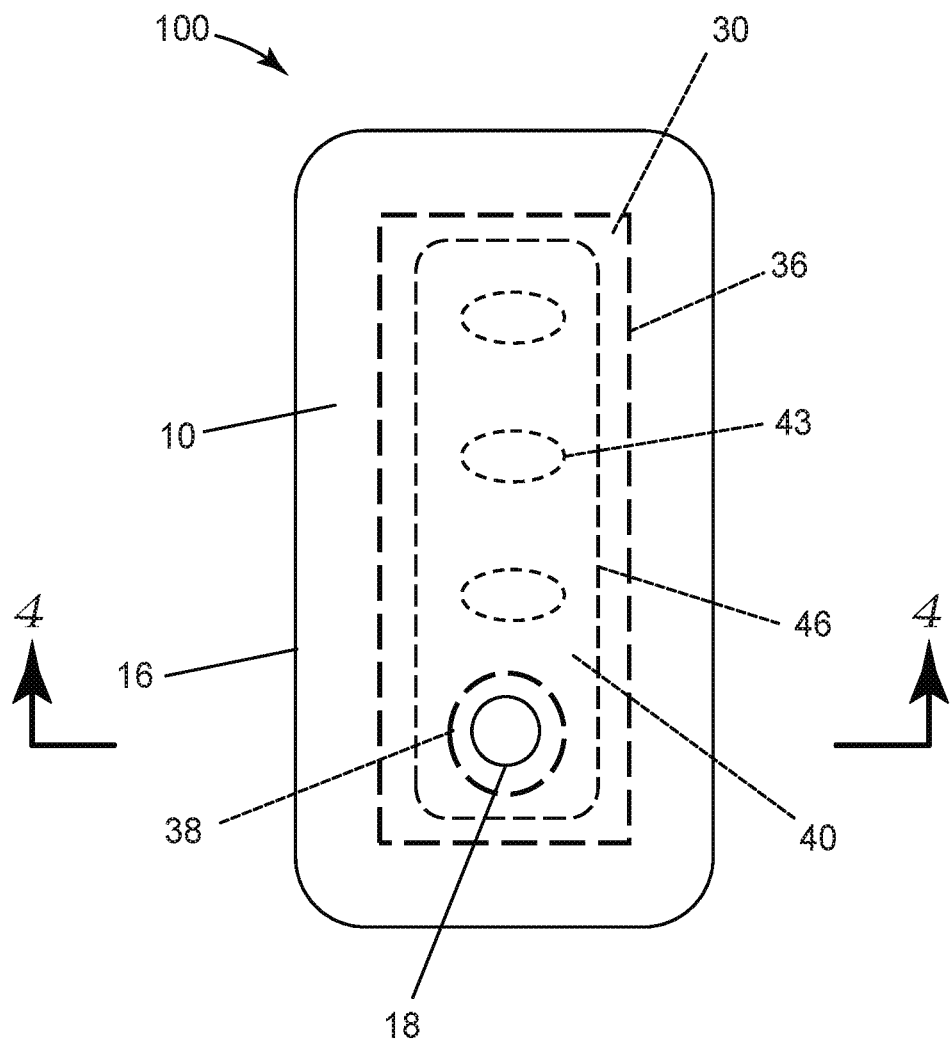
FIG. 1 is a schematic plan view of one embodiment of a wound dressing with an optional perforated layer according to the present disclosure.
Figure 2:
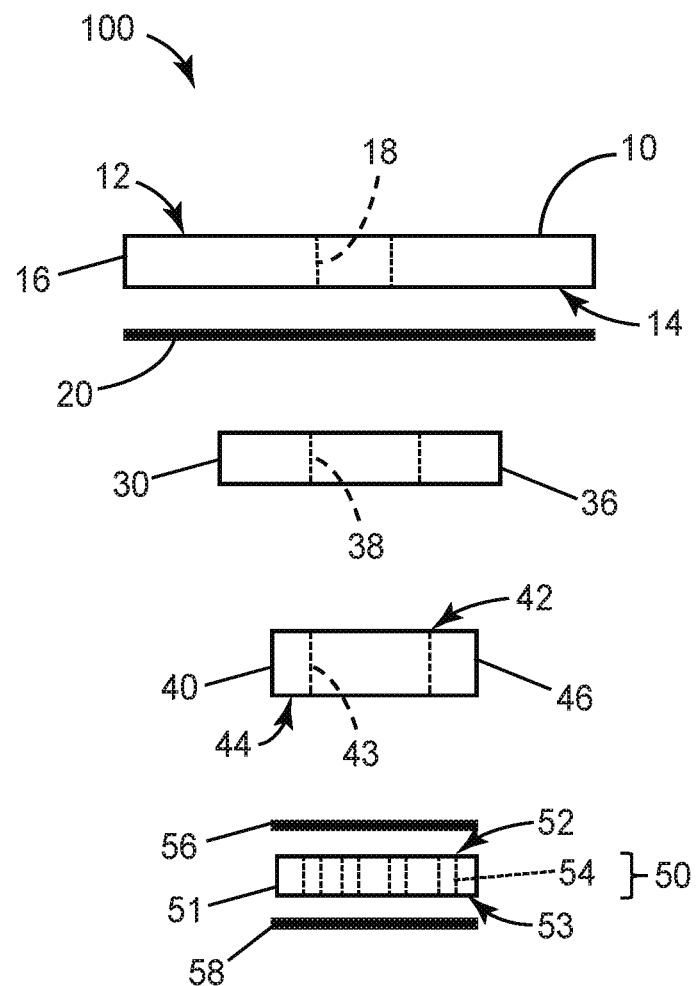
FIG. 2 is an exploded side view of the wound dressing of FIG. 1.

Turning now to the drawings, FIG. 1 is an exploded side view and FIG. 2 is a plan view of one embodiment of a wound dressing 100 according to the present disclosure. The dressing 100 comprises a backing layer 10, an absorbent adhesive gel 30 adhered to at least a portion of the moisture-transmissible backing layer 10, and a porous layer 40. In any embodiment, the dressing 100 optionally comprises a perforated layer 50. The wound dressing 100 can be formed in a variety of shapes including, for example, a circle, an oval, a trapezoid, a rectangle, and a square, which can include rounded corners for each of the various shapes.

The backing layer 10 has a first major surface 12, a second major surface 14 opposite the first major surface, a backing layer perimeter 16 that defines the edge of the backing layer, and an opening 18 that extends from the first major surface 12 to the second major surface 14. The backing layer 10 is made from a flexible material (e.g., a polymeric elastic film, an elastic non-woven fabric, or combinations thereof) that is compliant enough to conform to the anatomical contours of skin surfaces. The backing layer perimeter 16 defines outer edges of the backing layer 10.

Suitable backing layers 10 include, for example, nonwoven fibrous webs, woven fibrous webs, knits, films and other familiar backing materials. The preferred backing materials are translucent or transparent polymeric elastic films. Most preferably, the backing is a high moisture vapor permeable film backings. U.S. Pat. No. 3,645,835, the disclosures of which are hereby incorporated by reference, describe methods of making such films and methods for testing their moisture vapor permeability.

In any embodiment, the backing layer 10 has a thickness of about 15 μm to about 250 μm.

Adhered to (e.g., coated onto) at least a portion (e.g., a continuous portion that extends along the second major surface 14 proximate the entire backing layer perimeter 16) is a first adhesive 20. In use, the first adhesive 20 forms a seal (e.g., a liquid seal around the entire backing layer 16) between the backing layer 10 and the skin to which the dressing is applied.

Preferably, the backing layer/first adhesive composite should permit transmission of moisture vapor therethrough at a rate equal to or greater than human skin. Preferably, the uncoated film (i.e., the backing layer without the first adhesive coated thereon) transmits moisture vapor therethrough at a rate of at least 10 g/10 cm$^2$/24 hrs as measured by EN-13726-1:2002 Section 3.3. Even more preferably, the uncoated backing layer transmits moisture greater than 20 g/10 cm$^2$/24 hours. In any embodiment, the adhesive coated portions of the backing layer transmit moisture vapor at rate of at least 0.8 g/10 cm$^2$/24 hours, and preferably greater than 1.6 g/10 cm$^2$/24 hours.

The backing layer 10 is preferably conformable to anatomical surfaces. As such, when the backing layer is applied to an anatomical surface, it conforms to the surface even when the surface is moved. The preferred backing layer 10 is also conformable to animal anatomical joints. When the joint is flexed and then returned to its unflexed position, the backing layer stretches to accommodate the flexion of the joint, but is resilient enough to continue to conform to the joint when the joint is returned to its unflexed condition. Preferably, the backing layer has an ultimate elongation of greater than 200%. More preferably, the backing layer has an ultimate elongation of greater than 400%.

A description of this characteristic of backing layers preferred for use with the wound dressing of the present disclosure can be found in issued U.S. Pat. Nos. 5,088,483 and 5,160,315, the disclosures of which are hereby incorporated by reference in their entirety. Particularly preferred backing layers are elastomeric polyurethane, co-polyester, or polyether block amide films. These films combine the desirable properties of resiliency, high moisture vapor permeability, and transparency found in preferred backing layers.

While any pressure sensitive adhesive can be used for the first adhesive 20, preferred adhesives include a pressure sensitive adhesive that is reasonably skin compatible, such as soft silicone gel adhesives, Kraton® based adhesive, hydrocolloid adhesives, or the acrylate copolymers described in U.S. Pat. No. RE 24,906, the disclosure of which is hereby incorporated by reference in its entirety. Particularly preferred is a 97:3 iso-octyl acrylate:acrylamide copolymer. Also preferred is an 70:15:15 isooctyl acrylate: ethyleneoxide acrylate:acrylic acid terpolymer, as described in U.S. Pat. No. 4,737,410 (Example 31), the disclosure of which is hereby incorporated by reference in its entirety. Other useful adhesives for first adhesive 20 are described in U.S. Pat. Nos. 3,389,827, 4,112,213, 4,310,509, and 4,323, 557, the disclosures of which are hereby incorporated by reference in their entirety. Inclusion of medicaments or antimicrobial agents in the adhesive is also contemplated, as described in U.S. Pat. Nos. 4,310,509 and 4,323,557 both of which are hereby incorporated by reference in their entirety.

The preferred pressure sensitive adhesives for first adhesive 20 described above preferably transmit moisture vapor at rate greater to or equal to that of human skin. While such a characteristic can be achieved through the selection of an appropriate adhesive or through use of a nonwoven (e.g., melt blown) adhesive (as described in U.S. Pat. Nos. 6,171, 985, 6,368,687, and PCT Publication No. WO 99/27975 (all of which are incorporated herein by reference in their entirety)), it is also contemplated in the wound dressings of the present disclosure that other methods of achieving a high relative rate of moisture vapor transmission may be used, such as pattern coating (not shown) the first adhesive on the backing layer. In addition, this adhesive has low absorbency (i.e., less than 25% its dry weight, and preferably less than 10% its dry weight) when submerged in isotonic saline at 37 Celsius for 24 hours.

The absorbent adhesive gel 30 is adhered to at least a portion of the second major surface 14 of the backing layer 10. The absorbent adhesive gel 30 comprises an absorbent adhesive gel perimeter 36 that defines the outer edge of the adhesive gel perimeter. The absorbent adhesive gel perimeter 36 is spaced apart from the backing layer perimeter 16. Thus, in use, when the first adhesive 20 of the backing layer 10 is applied to a treatment surface (not shown), the backing layer 10 overlaps 100 percent of the absorbent adhesive gel perimeter 36. As used herein, a first piece (e.g. the backing layer) can be said to "overlaps" or "overlie" a second piece (e.g., the absorbent adhesive gel) if it covers a portion of either the second piece, or a portion of some third piece that is covered along its opposite side by the second piece. In other words, one piece can "overlap" or "overlie" another piece even though separated by a third piece.

Optionally, the absorbent adhesive gel comprises a second opening 38. When present, the second opening 38 preferably is spaced apart from the absorbent adhesive gel perimeter. At least a portion of the first opening 18 of the backing layer 10 does not have absorbent adhesive gel 30 between it and the porous layer (e.g., the first opening is located at a portion where there is no absorbent adhesive gel between the first opening and the porous layer, as shown in the wound dressing 102 of FIG. 3A; or the first opening overlaps at least a portion of a second opening 38 in the absorbent adhesive gel, as shown in FIG. 3B). In any embodiment, the first and second openings can be coextensive. This configuration facilitates liquid flow from the (skin) treatment surface through the porous layer 40 and out of the backing layer 10 via the first opening 18. The absorbent adhesive gel 30 can be relatively thin. In any embodiment, the absorbent adhesive gel has a thickness of about 0.2 mm to about 4.0 mm. In any embodiment, the absorbent adhesive gel has a thickness of about 0.4 mm to about 3 mm.

The absorbent adhesive gel 30 is capable of absorbing and retaining an aqueous liquid having an ionic strength similar to blood. Thus, this property can be tested easily by quantifying the absorbance of physiological saline. In any embodiment, the absorbent adhesive gel is capable of absorbing at least 0.4 times its dry weight; preferably, at least 1.0 times its dry weight; more preferably, greater than or equal to 1.5 times its dry weight; even more preferably, greater than or equal to 4 times its dry weight when contacted with an isotonic saline solution at 37° C. for 24 hours. The gel also has high moisture retention in that it will retain greater than 50% of what it absorbs (i.e., residual absorbent capacity) when externally compressed with 40 mm Hg pressure.

In any embodiment, the absorbent adhesive gel 30 can comprise a hydrogel that includes polyglycerol-3, cross-linked polyvinylpyrrolidone, and/or hydroxypropyl guar. Nonlimiting examples of suitable absorbent adhesive hydrogels and methods of making said absorbent adhesive hydrogels are described in U.S. Patent Application No. 2009/0187130, which hereby is incorporated by reference in its entirety. Optionally, the absorbent adhesive gel may comprise an antimicrobial agent such as, for example an antimicrobial biguanide (e.g., chlorhexidine gluconate).

Suitable hydrogel compositions include, for example, a natural hydrogel, such as pectin, gelatin, or carboxymethylcellulose (CMC) (Aqualon Corp., Wilmington, Del.), a semi-synthetic hydrogel, such as cross-linked carboxymethylcellulose X4ink CMC) (e.g. Ac-Di-Sol; FMC Corp., Philadelphia, Pa.), a synthetic hydrogel, such as cross linked polyacrylic acid (PAA) (e.g., CARBOPOL™ No. 974P; B. F. Goodrich, Brecksville, Ohio), or a combination thereof.

In most embodiments, the hydrogel adhesive comprises a swellable, crosslinked poly(N-vinyl lactam), a swelling agent and a modifying polymer present in an amount sufficient to form a cohesive, pressure-sensitive adhesive composition as described further in U.S. Patent Publication No. 2004/0247655. The amount of swelling agent to be mixed with the crosslinked swellable poly(N-vinyl lactam) can range from about 50 to about 90 weight percent of the composition. Consequently, exclusive of any biocompatible and/or therapeutic and/or ionically conductive materials to be added to the composition, the weight percent of the swellable poly(N-vinyl lactam) can be from about 10 to about 50 weight percent. When the poly(N-vinyl lactam) is poly(N-vinyl pyrrolidone), the weight percent of poly(N-vinyl pyrrolidone) can range from about 15 to about 45 percent. In particular embodiments, the poly (N-vinyl pyrrolidone) can range from about 18 percent to about 35 percent.

In most embodiments, the hydrogel adhesive composition of the present invention comprises a swellable, poly(N-vinyl lactam) that is radiation-crosslinked, typically while the lactam is in a solid form. In other embodiments, the poly (N-vinyl) lactam is crosslinked by free-radical polymerization, either in bulk or in solution, of a precursor containing an N-vinyl lactam monomer, optionally other monomers, and a crosslinking compound as described in U.S. Pat. No. 4,931,282. Poly(N-vinyl lactam) useful in an absorbent adhesive of present disclosure can be provided in any form susceptible to being crosslinked such as the solid forms described in U.S. Pat. Nos. 4,931,282; 5,225,473; and 5,389,376. Typically, the poly(N-vinyl lactam) is a homopolymer of N-vinyl-2-pyrrolidone.

After exposure to ionizing radiation, poly(N-vinyl lactam) can have a swelling capacity in water of at least about 15, typically at least about 30, and often at least about 40 as described in U.S. Pat. No. 5,409,966, which is incorporated herein by reference in its entirety. Poly(N-vinyl lactam) in any solid form may be crosslinked for use when subjected to ionizing radiation from a high-energy source.

The modifying polymer is present in the hydrogel adhesive composition to maintain and/or increase cohesiveness while reducing adhesiveness. When added with the swelling agent, the modifying polymer becomes solubilized or suspended in the swelling agent. Typically, the modifying polymer will form a viscous solution or viscous gel when combined with the swelling agent in a ratio of modifying polymer to swelling agent of 1:9.

The choice of swelling agent typically will determine the appropriate modifying polymer to accomplish a reduction in adhesion while maintaining or improving cohesion of the adhesive composition. Modifying polymers that are poorly solubilized in one swelling agent may be highly swollen in a different swelling agent for use in the present invention. In some embodiments, examples of suitable modifying swellable polymers include, but are not limited to, polysaccharides, polysaccharide derivatives, acrylates, acrylate derivatives, cellulose, cellulose derivatives, and combinations thereof.

In particular embodiments, modifying swellable polymers for use in the present invention are hydroxypropyl guar; guar gum; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and diallyldimethyl ammonium chloride; and derivatives and combinations of the foregoing.

The amount of modifying polymer can range up to about 50 weight percent of the composition. Consequently, exclusive of any biocompatible and/or therapeutic and/or ionically-conductive materials to be added to the composition, the weight percent of the modifying polymer can be from about 0.1 to about 40 weight percent. When the modifying polymer is hydroxypropyl guar, the weight percent of hydroxypropyl guar can range from about 1 to about 20 percent.

The hydrogel adhesive composition also comprises a swelling agent which can swell both the crosslinked poly (N-vinyl lactam) polymer and the modifying polymer, and which is biocompatible with human skin. Nonlimiting examples of swelling agents useful to swell the poly(N-vinyl lactam) include monohydric alcohols (e.g., ethanol and isopropanol), polyhydric alcohols, (e.g., ethylene glycol, propylene glycol, polyethylene glycol (Molecular Weight between 200 and 600) and glycerin), ether alcohols (e.g., glycol ethers), other polyol swelling agents which do not cause skin irritation or toxic reaction, and water.

Depending on the ultimate use desired for the hydrogel adhesive composition, non-volatile and/or volatile swelling agents may be used. One suitable swelling agent may comprise volatile swelling agent and non-volatile swelling agent, such as a mixture of glycerin or polyethylene glycol with water. In some embodiments, non-volatile swelling agents may be used by themselves such as, for example, glycerin or polyethylene glycol. Likewise, volatile swelling agents such as water may be used by themselves in the compositions of the invention. For this invention, "essentially non-volatile" means that a swelling agent as used in the present invention will render the adhesive polymer, such as radiated poly(N-vinyl lactam), sufficiently cohesive and pressure sensitive adhesive, such that less than ten percent (10%) of a given volume of nonvolatile swelling agent evaporates after exposure to processing or storage conditions.

The swelling agent can be added in an amount ranging from about 50 to about 90 weight percent of the hydrogel adhesive composition and preferably from about 60 to about 80 weight percent. In some embodiments, glycerin and polyethylene glycol are chosen to be the essentially non-volatile swelling agent. Both glycerin and polyethylene glycol can comprise up to 100 weight percent of the swelling agent.

The absorbent adhesive gel 30 is useful for containing a number of substances, optionally including antimicrobial agents, drugs for transdermal drug delivery, chemical indicators to monitor hormones or other substances in a patient, etc.

The absorbent adhesive gel can deliver an antimicrobial agent to the skin, reducing the likeliness of an infection to a percutaneous device or to treat infections of the skin or wounds. In most embodiments, the antimicrobial agent is added in levels up to 10% by weight of the total composition.

There are numerous biologically active materials, which include antimicrobial agents. Examples of antimicrobial agents include parachlorometaxylenol; triclosan; chlorhexidine and its salts such as chlorhexidine gluconate, polyhexamethylene biguanide and its salts such as poly hexamethylene biguanidine chloride, iodine, idodophors, fatty acid monoesters; poly-n-vinyl pyrrolidone-iodophors; silver oxide, silver and its salts, peroxides (e.g. hydrogen peroxide), antibiotics (e.g. neomycin, bacitracin, and polymyxin B). Other suitable antimicrobial agents are those listed in U.S. Patent Publication No. 2004/0247655.

A method of preparing a hydrogel adhesive composition of the present disclosure comprises mixing crosslinked poly(N-vinyl lactam) with a swelling agent and a modifying polymer, and other additives in a solvent which is may be somewhat volatile at or above ambient temperatures. Typically, the swelling agent, modifying polymer, and other additives, such as antimicrobial agents, are in essentially unirradiated form. Examples of suitable volatile solvents include water, ethanol, methanol, and isopropanol. A quantity of the resulting suspension is then cast onto a surface of a substrate, such as a release liner or a backing material and then stored. The volatile solvent is evaporated by heating such as by the application of microwave energy, infrared energy, or by convective air flow or the like, in order to form a cohesive, pressure-sensitive adhesive composition on the substrate. Often, a drying oven heated to about 65 degree C. may be employed for the evaporation step. A product release liner can optionally be laminated over the exposed surface of the composition to protect it from contamination.

In any embodiment, the absorbent adhesive gel 30 can comprise a hydrocolloid that contains polyisobutylene, a polyisoprene based polymer, a soluble absorbent, an insoluble absorbent, and a tackifier. Suitable hydocolloid compositions include, for example, 20-40% by weight of polyisobutylene (OPPANOL from BASF), 15-40% of a polyisprene based polymer, and a 15-45% by soluble and insoluble absorbents such as carboxymethylcellulose (CMC) (Aqualon Corp., Wilmington, Del.) and cross-linked carboxymethylcellulose X4ink CMC) (e.g. Ac-Di-Sol; FMC Corp., Philadelphia, Pa.), respectively, and less than 15% by weight of a tackifier such as WINGTACK 95 (Sartomer Co., Exton, Pa.).

In some embodiments, the hydrocolloid comprises a crosslinked hydrophobic silicone gel with soluble and/or insoluble absorbents dispersed therein. The absorbent content should be 15-45% by weight.

In addition to being capable of absorbing aqueous liquid, the absorbent adhesive gel 30 of the present disclosure, when adhered to the backing layer 10, is moisture transmissive. Thus, in any embodiment, the backing layer 10 with the absorbent adhesive gel 30 adhered thereto has a Moisture Vapor Transmission Rate (MVTR) ≥1 $g/10\ cm^2/24$ hours, as measured by EN-13726-1:2002 Section 3.3. Preferably, this Moisture Vapor Transmission Rate is greater than 3 $g/10\ cm^2/24$ hours. Advantageously, because the wound dressing 100 has a moisture vapor-transmissive backing layer and a moisture vapor-transmissive absorbent adhesive gel, moisture can be transported away from the wound site and out of the dressing 100 by two means: 1) passage out of the dressing (in the liquid state) through the first opening and out of the dressing, and 2) passage through the absorbent adhesive gel and out of the intact backing layer (in the vapor state). A high moisture vapor transmission rate through the gel and backing layer is important because it reduces the size of the canister needed for collection of wound exudate when using vacuum therapy for wounds. A high MVTR gel and backing is especially useful in the embodiment when the vacuum source is a created mechanically using constant force springs such as that used in the SNaP® Wound Care System (Spiracur, Inc.; Sunnyvale, Calif.). The high MVTR gel/backing system prolongs the effective life of a mechanical vacuum system because fluid is removed via evaporation and does not fill the canister or cartridge.

In any embodiment, before applying the wound dressing of the present disclosure to a treatment site, the absorbent adhesive gel comprises less than 40% (w/w) water. In any embodiment, before applying the wound dressing of the present disclosure to a treatment site, the absorbent adhesive gel comprises less than 25% (w/w) water. Preferably, before applying the wound dressing of the present disclosure to a treatment site, the absorbent adhesive gel comprises less than 10% (w/w). The use of an absorbent adhesive gel comprising <40% (w/w) water, <25% (w/w) water, or <10% (w/w) reduces the need for specialized packaging that would otherwise be needed to preserve the water in the gel during storage before use.

The elastic properties (e.g., as indicated by the storage modulus (G')) of the absorbent adhesive gel is selected so that, within the range of thicknesses of the absorbent adhesive gel, the wound dressing is conformable, yet of high integrity so that it won't readily fall apart when stretched. In any embodiment, before applying the wound dressing of the present disclosure to a treatment site, the absorbent adhesive gel has a storage shear modulus between about 5,000 pascals and about 50,000 pascals at 24° C. at a shear rate of 1 rad/sec. Preferably between 10,000 pascals and about 30,000 pascals.

In addition, the loss modulus (G") indicates the viscous response of the absorbent adhesive gel 30. In any embodiment, before applying the wound dressing of the present disclosure to a treatment site, the absorbent adhesive gel has a loss shear modulus between about 2,000 pascals and about 20,000 pascals (inclusive) at 24° C. at a shear of 1 rad/sec. Preferably, between about 3,000 pascals and about 15, 000 pascals, inclusive. Advantageously, an absorbent adhesive gel having a loss modulus G" between about 2,000 pascals and about 20,000 pascals (inclusive) at 24° C. at a shear of 1 rad/sec is sufficiently soft to create a good vacuum seal on skin but not so soft that flows readily and easily loses its integrity.

Returning to the drawings, a wound dressing 100 according to the present disclosure comprises a porous layer 40. The porous layer 40 has a first side 42, a second side 44, and a porous layer perimeter 46 that defines the outer edge of the porous layer, which further defines a porous layer area. The first side 42 of the porous layer 40 is adhered to the absorbent adhesive gel 30. In any embodiment, at least 50% of the porous layer perimeter is overlapped by the absorbent adhesive gel. In any embodiment, more than 50% of the porous layer perimeter is overlapped by the absorbent adhesive gel. In any embodiment, at least 60% of the porous layer perimeter is overlapped by the absorbent adhesive gel. In any embodiment, at least 70% of the porous layer perimeter is overlapped by the absorbent adhesive gel. In any embodiment, at least 75% of the porous layer perimeter is overlapped by the absorbent adhesive gel. In any embodiment, at least 80% of the porous layer perimeter is overlapped by the absorbent adhesive gel. In any embodiment, at least 85% of the porous layer perimeter is overlapped by the absorbent adhesive gel. In any embodiment, at least 90% of the porous layer perimeter is overlapped by the absorbent adhesive gel. In any embodiment, at least 95% of the porous layer perimeter is overlapped by the absorbent adhesive gel. In any embodiment, 100% of the porous layer perimeter is overlapped by the absorbent adhesive gel. Preferably, the gel extends past the porous layer perimeter (i.e., toward the backing layer perimeter) by at least 3 mm and more preferably at least 5 mm.

In addition to providing a good vacuum seal to skin, the absorbent adhesive gel also acts as a reservoir for fluid such that it will take up moisture from the porous layer which facilitates keeping the porous layer free from liquid. The less liquid in the porous layer, the lower the pressure drop across the dressing when under vacuum. This pressure drop is very noticeable when the porous layer is saturated with liquid.

The porous layer 40 is configured to facilitate passage of fluid (e.g., blood or other fluids leaking from a wound site such as an incisional wound, for example) through the porous layer to the first opening 18 of the backing layer 10. In any embodiment, the porous layer 40 can comprise open-cell foam, a woven fabric (e.g., gauze), or a nonwoven fabric. Multi-layer porous polymer films would also be acceptable.

In any embodiment, the porous layer 40 can be combination of layers of material. For example, a non-woven fabric laminated (or otherwise attached) to a foam could be considered the porous layer. In a preferred embodiment, a non-woven fabric with a porous film (macroporous or microporous) laminated to one or both sides of it, that is then laminated to an open cell foam can function as a good porous layer because the multiple layers enables fluid to readily pass through the porous layer and because it is more resistant to collapse under vacuum.

In any embodiment, the porous layer 40 optionally comprises one or more open area 43. In any embodiment, the porous layer 40 optionally comprises a plurality of open areas 43. The open area 43 is a through-hole that is substantially larger than the pores of the porous layer 40. In any embodiment, a sum of the open areas 43 has an area that is greater than or equal to 5 percent and less than or equal to 50 percent of the porous layer area. In any embodiment, the sum of the open areas 43 has an area that is greater than or equal to 5 percent and less than or equal to 20 percent of the porous layer area. Advantageously, the open areas 43 function to facilitate visualization of the wound site without removing the dressing.

Preferably, the open areas should be large enough such that the adhesive gel will conform to the sides of the open area and make contact with the skin or the perforated layer upon application of vacuum. In any embodiment, the holes are ovals, circles, squares, rectangles, or diamond in shape, for example, and a hole is at least 0.4 $cm^2$ in area, and preferably greater than 0.75 $cm^2$ in area, and most preferably greater than 1.5 $cm^2$ in area. The area of an individual hole should not exceed 13 $cm^2$ as too large of an open area reduces the available area of porous layer for communicating negative pressure to the wound and for evacuating fluid away from the wound.

The open areas 43 can take the form of any shape. The illustrated embodiment of the wound dressing 100 of FIGS. 1 and 2 comprises a plurality of oval-shaped open areas. Non-limiting examples of shapes that are suitable for open areas 43 include circles, triangles, squares, rectangles, and other polygons.

In any embodiment, a wound dressing 100 of the present disclosure optionally comprises a perforated layer 50. The perforated layer 50 comprises a substrate 51 (e.g., a polymeric film substrate, a foam, a non-woven fabric, a woven fabric, or a combination of any two or more of the foregoing materials) with a first surface 52, a second surface 53, a perforated layer perimeter 56, and a plurality of perforations 54 extending therethrough. The perforations 54 provide a liquid pathway for exudate from the wound to pass through the substrate 51 and into the porous layer 40. The first surface 51 of the perforated layer 50 is adhered to the second side 44 of the porous layer 40 via a second adhesive 56, which may be coated onto the perforated layer 50. The second adhesive may be any suitable adhesive for adhering the perforated layer 50 to the porous layer 40. Optionally, the perforated layer 50 may comprise a third adhesive 58 coated thereon. The third adhesive 58 can provide additional securement of the wound dressing 100 to the treatment site (skin). In any embodiment, the third adhesive 58 can comprise a hydrophobic soft silicone adhesive. The second adhesive 56 and third adhesive 58 can be coated onto the perforated layer 50 prior to perforating the substrate and, thus, the second and third adhesive also comprise perforations. Alternatively or additionally, the second adhesive 56 and third adhesive 58 can be pattern coated onto the substrate 51. Advantageously, the perforations 54 in the perforated layer 50 not only provide a pathway for moisture transmission to the porous layer 40, they also render the perforated layer 50 highly conformable to the anatomical surfaces of various wound sites. The perforated layer does not have to be coextensive with the perimeter of porous layer or the open areas.

Preferably the third adhesive 58 is a soft silicone adhesive and is greater than 50 microns thick; more preferably, greater than 75 microns thick. The third adhesive 58 provides added securement of the wound dressing to the tissue and provides improved vacuum sealing properties at the skin/adhesive interface proximate the porous layer. Preferably, the adhesion to steel of this porous layer with a soft silicone adhesive layer is less than the adhesion to steel of the absorbent adhesive gel and/or the adhesive layer coated on the backing. In addition, the third adhesive has low absorbency in isotonic saline at 37 Celsius for 24 hours. (i.e., less than 25% of its dry weight, and preferably less than 10% its dry weight).

In any embodiment of a wound dressing of the present disclosure, the dressing further comprises a vacuum port (not shown in FIGS. 1-3). The vacuum port is a structure that permits operatively coupling the wound dressing to a source of negative pressure, as shown in FIG. 4. The vacuum port can be any suitable vacuum port known in the art that can be sealingly attached (e.g., via a pressure sensitive adhesive, a secondary transparent adhesive/film dressing, or a heat seal) to the backing layer.

Although the illustrated embodiment of FIGS. 1 and 2 show a wound dressing 100 wherein the absorbent adhesive gel perimeter 36 completely overlaps the porous layer perimeter 46, it is contemplated that, in certain embodiments, the absorbent adhesive gel perimeter 36 does not overlap 100% of the porous layer perimeter 46, as discussed above. FIG. 3 shows one embodiment of a wound dressing 101 wherein the absorbent adhesive gel perimeter 36 of the absorbent adhesive gel 30 does not completely overlap the porous layer perimeter 46 of the porous layer 40. In this embodiment, the backing layer perimeter 16 of the backing layer 10 completely overlaps both the absorbent adhesive gel perimeter 36 and the porous layer perimeter 46. Also shown in FIG. 3A is the first opening 18 of the backing layer 10 and the second opening 38 of the absorbent adhesive gel 30.

In use, the wound dressing is applied to a treatment site with the adhesive side (i.e., of the second major surface) of the backing layer facing the skin. FIG. 4 shows a side view, partially in section, of one embodiment of a wound dressing 103 applied to the surface of skin 5 at a treatment site. The wound dressing 103 is identical to the wound dressing 100 of FIG. 1 except that, in addition to comprising a backing layer 10 with a first opening (not shown), an absorbent adhesive gel 30 comprising a second opening 38, a porous layer 40 with a plurality of open areas 43, and a perforated layer 50; the wound dressing 103 further comprises a vacuum port 70. The vacuum port 70 is operatively coupled to a source of negative pressure 80 (e.g., a vacuum pump (not shown)) via tubing 82. The first adhesive (not shown) on the second major surface 14 forms a liquid-tight seal on the skin 5.

In any embodiment, a wound dressing comprising a vacuum port according to the present disclosure can be operatively connected to a source of vacuum. The source of vacuum can be a mechanical pump, for example. In any embodiment, the source of vacuum can be a mechanically-powered, portable vacuum pump. In any embodiment, the mechanically-powered vacuum source comprises one or more constant force spring.

EXEMPLARY EMBODIMENTS

Embodiment A is a wound dressing, comprising:
a moisture-transmissible backing layer having a first major surface, a second major surface, a backing layer perimeter, and a first opening;
wherein the second major surface has a first adhesive disposed thereon proximate the backing layer perimeter;
an absorbent adhesive gel adhered to at least a portion of the second major surface of the backing layer, the absorbent adhesive gel comprising an adhesive gel perimeter; and
a porous layer having a first side, a second side, and a porous layer perimeter;
wherein the first side of the porous layer is adhered to the absorbent adhesive gel;
wherein the porous layer is configured to facilitate passage of fluid to the second opening;
wherein 100% of the adhesive gel perimeter is overlapped by the backing layer;
wherein at least 50% of the porous layer perimeter is overlapped by the absorbent adhesive gel.

Embodiment B is the wound dressing of Embodiment A, wherein the absorbent adhesive gel further comprises a second opening.

Embodiment C is the wound dressing of Embodiment B, wherein at least a portion of the first opening overlaps at least a portion of the second opening.

Embodiment D is the wound dressing of any one of the preceding Embodiments, wherein the absorbent adhesive gel has a thickness of about 0.2 mm to about 4.0 mm.

Embodiment E is the wound dressing of Embodiment D, wherein the absorbent adhesive gel has a thickness of about 0.5 mm to about 4.0 mm.

Embodiment F is the wound dressing of Embodiment E, wherein the absorbent adhesive gel has a thickness of about 0.5 mm to about 3.0 mm.

Embodiment G is the wound dressing of any one of the preceding Embodiments, wherein the absorbent adhesive gel comprises less than or equal to about 40% (w/w) water.

Embodiment H is the wound dressing of any one of the preceding Embodiments, wherein the absorbent adhesive gel comprises less than or equal to about 25% (w/w) water.

Embodiment I is the wound dressing of Embodiment G or Embodiment H, wherein the absorbent adhesive gel comprises less than or equal to about 10% (w/w) water.

Embodiment J is the wound dressing of any one of the preceding Embodiments:
wherein the porous layer has a porous layer area defined by the porous layer perimeter;
wherein the porous layer comprises at least one open area;
wherein the sum of the open areas is greater than or equal to 5% and less than or equal to 50% of the porous layer area.

Embodiment K is the wound dressing of any one of the preceding Embodiments,
wherein the porous layer has a porous layer area defined by the porous layer perimeter;
wherein the porous layer comprises a plurality of open areas, each open area being greater than or equal to 5% and less than or equal to 50% of the porous layer area.

Embodiment L is the wound dressing of Embodiment J or Embodiment K, wherein sum of the open areas is greater than or equal to 5% and less than or equal to 20% of the porous layer area.

Embodiment M is the wound dressing of any one of the preceding Embodiments, wherein the dressing further comprises a perforated layer adhered to the second side of the porous layer.

Embodiment N is the wound dressing of Embodiment M, wherein the perforated layer comprises a perforated polymeric substrate.

Embodiment O is the wound dressing of Embodiment M or Embodiment N, wherein the perforated layer has a first major surface facing the second side of the porous layer and a second major surface opposite the first major surface, wherein the second major surface includes a silicone adhesive.

Embodiment P is the wound dressing of Embodiment O, wherein the silicone adhesive has a thickness greater than or equal to 50 microns.

Embodiment Q is the wound dressing of Embodiment O, wherein the silicone adhesive has a thickness greater than or equal to 75 microns.

Embodiment R is the wound dressing of any one of Embodiments O through Q, wherein adhesion to steel of the absorbent adhesive gel adhered to the backing layer is greater than adhesion to steel of the silicone adhesive adhered to the porous layer.

Embodiment S is the wound dressing of any one of Embodiments O through R, wherein adhesion to steel of the absorbent adhesive gel adhered to the backing layer is greater than adhesion to steel of the first adhesive adhered to the backing layer.

Embodiment T is the wound dressing of any one of the preceding Embodiments, wherein the backing layer comprises a polymeric elastic film, an elastic non-woven fabric, or combinations thereof.

Embodiment U is the wound dressing of Embodiment T, wherein the backing layer is about 15 µm to about 250 µm thick.

Embodiment V is the wound dressing of any one of the preceding Embodiments, wherein the backing layer has a Moisture Vapor Transmission Rate ≥10 g/10 cm$^2$/24 hours, as measured by EN-13726-1:2002 Section 3.3.

Embodiment W is the wound dressing of any one of the preceding Embodiments, wherein the backing layer with the absorbent adhesive gel adhered thereto has a Moisture Vapor Transmission Rate ≥1 g/10 cm$^2$/24 hours, as measured by EN-13726-1:2002 Section 3.3.

Embodiment X is the wound dressing of any one of the preceding Embodiments, wherein the absorbent adhesive gel has a shear modulus between about 5,000 pascals and about 50,000 pascals at 24° C. at a shear of 1 rad/sec.

Embodiment Y is the wound dressing of any one of the preceding Embodiments, wherein the absorbent adhesive gel has a loss shear modulus between about 2,000 pascals and about 20,000 pascals at 24° C. at a shear of 1 rad/sec.

Embodiment Z is the wound dressing of any one of the preceding Embodiments, wherein the absorbent adhesive gel further comprises an antimicrobial agent.

Embodiment AA is the wound dressing of any one of the preceding Embodiments, wherein the porous absorbent layer comprises open-cell foam, a woven fabric, or a nonwoven fabric, a plurality of layers of porous film, or a combination of two or more of the foregoing materials.

Embodiment AB is the wound dressing of any one of the preceding Embodiments, wherein the absorbent adhesive gel is capable of absorbing ≥1.5 times its dry weight when contacted with an isotonic saline solution at 37° C. for 24 hours.

Embodiment AC is the wound dressing of any one of the preceding Embodiments, further comprising a vacuum port.

Embodiment AD is the wound dressing of Embodiment AB, further comprising a mechanically-powered vacuum source.

Embodiment AE is the wound dressing of Embodiment AC, wherein the mechanically-powered vacuum source comprises one or more constant force spring.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Adhesion to Steel Test.

The adhesion to steel test was conducted using 304 AISI stainless steel plates with a bright annealed finish. Dimensions of the plates were 51 mm×127 mm×1.6 mm. The test surfaces was cleaned prior to each test one time using a disposable laboratory wipe saturated with isopropanol and three times with a disposable laboratory wipe saturated with n-heptane. The surface was allowed to dry prior to placing the sample on the test surface. The length of the test sample was 1" wide. Prior to measuring the adhesive force, the adhesive side of the sample was manually pressed against the steel plate and the nonadhesive side of the sample was rolled with a roller once in each direction to press the adhesive side against the plate. The roller had a total diameter of 3.75" (95 mm), a face width of 1.75" (44 mm), and it was covered with approximately 0.25" (6 mm) thickness of 75-85 durometer hardness rubber having an effective rolling weight of 4.5 pounds or 2043 grams. The rolling speed was approximately 50 mm/second. The sample was tested immediately after rolling using a 180 degree peel at a rate of 305 mm/min. Testing was conducted in a room at 25 Celsius and 50% relative humidity.

Fluid Management Test

Figure 5:
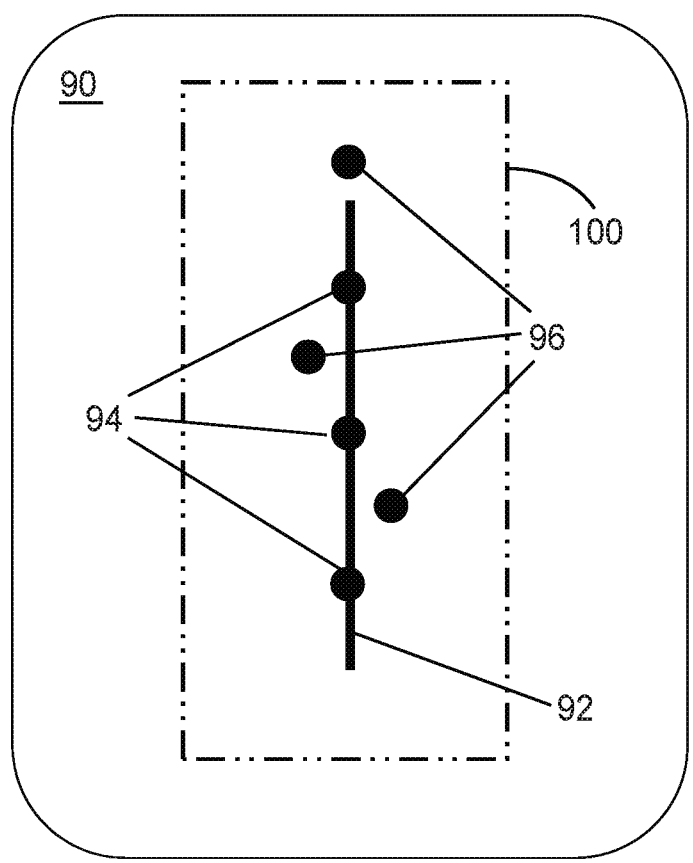
FIG. 5 is a schematic plan view of an apparatus for testing the vacuum seal and liquid management properties of a wound dressing according to the present disclosure.

A test apparatus was constructed to mimic an incisional wound. A schematic top view of the apparatus is shown in FIG. 5. The apparatus comprised a slit into which liquid was fed through three spaced-apart ports. The slit was intended to mimic an opening in the skin at the site of an approximately 150 mm long incision-type wound. The liquid fed through the spaced-apart ports was intended to mimic blood and/or serous fluid flow or leakage from an incision-type wound.

An aluminum table (12 mm thick plate) having a flat, top surface 90, FIG. 5) with three liquid feed ports 94 equally spaced within a slit 92 in the top 90 of the table. The slit 92 was 1 mm wide, 1.6 mm deep, and 152 mm long, and two of the liquid feed port holes 94 were spaced inward 19 mm from the their respective end of the slit with the remaining feed port hole 94 in the center of the slit. Three vacuum measurement ports 96 were located about 2 mm from the slit. One vacuum measurement port was located proximate one end of the slit, and the other two were on opposite sides of the slit about 50 mm from their respective slit ends. All ports extended completely through the table and the ports were threaded on the bottom of the table. Hose barb fittings were connected to both the feed ports and the vacuum measurement ports at the bottom of the table for easy connection with appropriate tubing.

In use, fluid was fed to each of the feed ports at the bottom of the aluminum table via a three syringes disposed in a syringe pump (Model NE-1600; New Era Pump Systems, Inc.; Farmingdale, N.Y.). Vacuum was measured using pressure transducers from Omega Engineering (Stamford, Conn.). When testing examples with this apparatus, vacuum was applied through a port that was sealed to the top of the samples described in the examples using an ATMOS WOUND RX 041 vacuum unit (Allentown, Pa.). All experiments with this test apparatus were operated at ambient temperature (approximately 24 Celsius) and ambient humidity (35-65% Relative humidity). The vacuum measured was the pressure difference from atmospheric. For example, a reading of 120 mm Hg means that the pressure in the system or dressing was 120 mm Hg below atmospheric pressure.

The adhesive side of wound dressings made according to Example 1 were pressed against the surface of the test apparatus such that the absorbent foam layer of the wound dressings overlapped the slit, the liquid feed ports, and the vacuum measurement ports.

Example 1

An adhesive-coated backing layer (such as can be obtained from 3M Transparent TEGADERM™ Film Roll 16004; 3M Company, St. Paul, Minn.) was cut into a rectangle approximately 10.16 cm×27.94 cm. A 1.27 cm diameter hole was punched through the adhesive/film backing approximately 2.5" (6.35 cm) from one edge of the dressing, and approximately centered along the width of the adhesive film backing as shown in FIG. 1. The release liner protecting the adhesive was then removed.

A large absorbent adhesive gel was made using the method described in Example E3 of US2009/0187130, which is incorporated herein by reference in its entirety. The absorbent adhesive gel was cut into a rectangle of 57 mm×229 mm. A 38 mm diameter hole was punched out proximate an edge of the absorbent adhesive gel. The absorbent adhesive gel was then laminated to the adhesive side of the breathable backing layer such that a hole in the adhesive/film back was approximately centered with the hole in the absorbent adhesive gel.

A 3.3 mm thick absorbent polyurethane foam (used in the 90642 3M TEGADERM Silicone Foam Border dressing; foam available from 3M Company, St. Paul, Minn.) was laminated to an absorbent non-woven layer used in the 3M TEGADERM+Pad product line available from 3M Company (St. Paul, Minn.) using a layer of porous adhesive (approximately 25% open). An eight inch (20.3 cm) by two inch (5.1 cm) rectangle with rounded corners was cut out of this foam/non-woven laminate to form the porous layer. Starting approximately 12.5 mm from one end of the porous layer, five oval-shaped (16 mm×25 mm) open areas were punched out of the rectangle. A perforated (ca. 15% open with 1.5 mm apertures) adhesive/polyurethane film/adhesive was then laminated to the foam side of the porous layer. The non-woven side of the porous layer was then centered over and laminated to the absorbent adhesive gel.

A vacuum port and tubing (removed from the dressing of the PICO Single Use Negative Pressure device obtained from Smith & Nephew, Andover, Mass.) was then attached with an adhesive to the opening in the backing layer of the constructed sample to ensure a leak free seal at the port.

The dressing was placed on the fluid management test apparatus (described above) with the adhesive side attached to the aluminum plate and the porous layer extended over all ports and the entire slit. The apparatus was connected to the vacuum system. A vacuum of 120 mm Hg from atmospheric was then pulled on the dressing. A total flow of 1 ml/hr of an aqueous solution containing 142 mmol/liter of sodium ions (from sodium chloride) and 2.5 mmol/liter of calcium ions (from calcium chloride) was then fed to the dressing. The data in Table 1 show the measured vacuum level in three identical dressings over time. The data demonstrate the presence of the absorbent adhesive gel helps minimize pressure drop in the dressing when the dressing is placed under vacuum and then held for periods up to about 21½

TABLE 1

Average pressure below atmospheric pressure in a dressing that comprises an absorbent adhesive gel as described herein. The test was conducted under the conditions described in the Wound Dressing Vacuum Test described herein.

| Time (hr) after applying vacuum | Average Pressure Below Atmospheric Pressure in the Dressing (mmHg) |
|---|---|
| 0 | 120 |
| 3.2 | 120 |
| 6.8 | 120 |
| 21.4 | 88 |

Comparative Example 1

Comparative Example 1 was constructed and tested in the same manner as Example 1 except that no absorbent adhesive gel was used. The data in Table 2 show the average measured pressure level below atmospheric pressure in the dressing over time.

TABLE 2

Average pressure below atmospheric pressure in dressing that does not comprise the absorbent adhesive gel as described herein. The test was conducted under the conditions described in the Wound Dressing Vacuum Test herein.

| Time (hr) after applying vacuum | Average Pressure Below Atmospheric Pressure in the Dressing (mmHg) |
|---|---|
| 0 | 120 |
| 3.3 | 120 |
| 6.4 | 120 |
| 22.4 | 40 |

The data in Tables 1 and 2 indicate the absorbent adhesive gel facilitates the removal of liquid from the porous layer and thereby minimizes the pressure drop in the dressing while permitting flow of the liquid away from the wound and through the porous layer.

Example 2

The rheological properties of the absorbent adhesive gel used in the dressings of Example 1 were measured as a function of drying temperature and time using a TA Instruments' ARES rheometer (Texas Instruments, New Castle, Del.). Samples of the absorbent adhesive gel were dried at 48.9° C. The shear measurements were taken at 24° C. and a frequency range from 0.1 to 500 rad/second. The adhesive gel sample was a 25 mm diameter circle with a thickness of 1.6 mm. The results for the dynamic shear viscosity are shown in Table 3. The results of the storage shear modulus (G'), and the loss shear modulus (G") measurements are shown in Table 4.

TABLE 3

Viscosity (poise) change with drying time at different shear rate.

| Drying Time | Viscosity (pascal · s) | | |
|---|---|---|---|
| (days) | 1 rad/sec | 10 rad/sec | 100 rad/sec |
| 0 | 171 | 28.66 | 6.3 |
| 1 | 215.9 | 37.35 | 8.73 |
| 7 | 266.3 | 50.04 | 13.33 |

TABLE 4

The change of the shear modulus (G') and the loss shear modulus (G") as a function of drying time and shear rate. All measured values are shown in pascals.

| | G' and G" as a function of shear rate | | | | | |
|---|---|---|---|---|---|---|
| Drying time | 1 rad/sec | | 10 rad/sec | | 100 rad/sec | |
| (days) | G' | G" | G' | G" | G' | G" |
| 0 | 15,000 | 5,300 | 24,500 | 12,500 | 50,000 | 38,000 |
| 1 | 20,000 | 7,200 | 32,500 | 16,000 | 65,000 | 55,000 |
| 7 | 23,500 | 9,800 | 42,000 | 24,300 | 91,000 | 93,000 |

Example 3

The test sample was prepared and tested the same as Example 1 except; 1) the liquid barrier contained in the vacuum port was removed, 2) the vacuum source was a SNaP® 125 mm Hg cartridge; 3) no open areas were cut out of the porous layer; and 4) the backing was a 23 micron thick urethane film with a 25 micron thick acrylate adhesive laminated to it. Two 5 cm×5 cm cutouts in the acrylate adhesive prior to lamination to the film were removed so that the absorbent adhesive gel was in direct contact with the urethane film in these areas in order to create a high MVTR areas of the dressing. The urethane film was made using Estane® 58237 polymer from Lubrizol Co; Wickliffe, Ohio). After 24 hours of testing (i.e., 24 cm$^3$ of solution fed to the dressing), the vacuum cartridge only changed volume by 8 cm$^3$. The average pressure in the dressing was 120 mm Hg below atmospheric pressure after 24 hours. This example illustrates the advantage of using a high MVTR absorbent gel and backing in order to reduce the cartridge size and enhance the vacuum capabilities of a mechanical vacuum source or a powered vacuum source.

Example 4

A 23 micron thick film of Estane 58237 was laminated to a discontinuous (pattern of approximately 1 mm diameter holes with 10% total open area) acrylate adhesive layer (described U.S. Pat. No. RE 24,906; a copolymer of isooctyl acrylate;acrylamide (97:3) with coating weight of 750 mg/200 cm$^2$). This film adhesive sample was equilibrated at 25 Celsius and 50% relative humidity. The adhesion to steel value of this sample was measured at 4 N/25 mm.

Example 5

A 23 micron thick film of Estane 58237 was laminated to a continuous layer of absorbent adhesive (as described in Example E3 of US2009/0187130) that was 1.75 mm thick. This film adhesive sample was equilibrated at 25 Celsius and 50% relative humidity. The adhesion to steel value of this sample was measured at 5.8 N/25 mm.

Example 6

A 30 micron thick urethane film (Texin 1209 from Bayer) was extruded onto a continuous acrylate adhesive whose coating weight was 550 mg/200 cm$^2$. A silicone gel adhesive was then coated at 0.1 mm thick and cured (as described in and WO2010/056543) onto the urethane film/adhesive laminate and a protective liner put onto this silicone adhesive. This multilayer laminate was then mechanically perforated (1.5 mm diameter holes; 20% open). The acrylate side of this laminate was then laminated to a polyurethane foam cut out of a 90642 3M™ TEGADERM™ Foam Silicone Border dressing. The adhesion to steel of the silicone side of this foam laminate was then tested at 25 Celsius and 50% relative humidity. The adhesion to steel value was measured at 2 N/25 mm.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A wound dressing, comprising:
   a moisture-transmissible backing layer having a first major surface, a second major surface, a backing layer perimeter, and a first opening;
   wherein the second major surface has an first adhesive disposed thereon proximate the backing layer perimeter;
   an absorbent adhesive gel adhered to at least a portion of the second major surface of the backing layer, the absorbent adhesive gel comprising an adhesive gel perimeter; and
   a porous layer having a first side, a second side, a porous layer perimeter, and at least one open area;
   wherein the first side of the porous layer is adhered to the absorbent adhesive gel;
   wherein the porous layer is configured to facilitate passage of fluid to the first opening;
   wherein 100% of the adhesive gel perimeter is overlapped by the backing layer;
   wherein at least 50% of the porous layer perimeter is overlapped by the absorbent adhesive gel.

2. The wound dressing of claim 1, wherein the absorbent adhesive gel further comprises a second opening.

3. The wound dressing of claim 1, wherein the absorbent adhesive gel has a thickness of 0.2 mm to 4.0 mm.

4. The wound dressing of claim 1, wherein the absorbent adhesive gel comprises less than 40% (w/w) water.

5. The wound dressing of claim 1:
   wherein the porous layer has a porous layer area defined by the porous layer perimeter;
   wherein the at least one open area that is greater than or equal to 5% and less than or equal to 50% of the porous layer area.

6. The wound dressing of claim 1:
   wherein the porous layer has a porous layer area defined by the porous layer perimeter;
   wherein the porous layer comprises a plurality of open areas, each open area being greater than or equal to 5% and less than or equal to 50% of the porous layer area.

7. The wound dressing of claim 5, wherein at least one of the open areas is greater than or equal to 5% and less than or equal to 20% of the porous layer area.

8. The wound dressing of claim 1, wherein the dressing further comprises a perforated layer adhered to the second side of the porous layer.

9. The wound dressing of claim 8, wherein the perforated layer has a first major surface facing the second side of the porous layer and a second major surface opposite the first major surface, wherein the second major surface includes a silicone adhesive.

10. The wound dressing of claim 9, wherein adhesion to steel of the absorbent adhesive gel adhered to the backing layer is greater than adhesion to steel of the silicone adhesive adhered to the porous layer.

11. The wound dressing of claim 9, wherein adhesion to steel of the absorbent adhesive gel adhered to the backing layer is greater than adhesion to steel is greater than adhesion to steel of the first adhesive adhered to the backing layer.

12. The wound dressing of claim 1, wherein the backing layer comprises a polymeric elastic film, an elastic nonwoven fabric, or combinations thereof.

13. The wound dressing of claim 1, wherein the backing layer has a Moisture Vapor Transmission Rate ≥10 g/10 cm$^2$/24 hours, as measured by EN-13726-1:2002 Section 3.3.

14. The wound dressing of claim 1, wherein the backing layer with the absorbent adhesive gel adhered thereto has a Moisture Vapor Transmission Rate ≥1 g/10 cm$^2$/24 hours, as measured by EN-13726-1:2002 Section 3.3.

15. The wound dressing of claim 1, wherein the absorbent adhesive gel has a shear modulus between 5,000 pascals and 50,000 pascals at 24° C. at a shear of 1 rad/sec.

16. The wound dressing of claim 1, wherein the absorbent adhesive gel has a loss shear modulus between about 2,000 pascals and about 20,000 pascals at 24° C. at a shear of 1 rad/sec.

17. The wound dressing of claim 1, wherein the absorbent adhesive gel further comprises an antimicrobial agent.

18. The wound dressing of claim 1, wherein the porous absorbent layer comprises open-cell foam, a woven fabric, a nonwoven fabric, porous films, or a combination thereof.

19. The wound dressing of, wherein the absorbent adhesive gel is capable of absorbing ≥1.5 times its dry weight when contacted with an isotonic saline solution at 37° C. for 24 hours.

20. The wound dressing of claim 1, further comprising a vacuum port.

* * * * *

UNITED STATES PATENT AND TRADEMARK OFFICE
CERTIFICATE OF CORRECTION

PATENT NO. : 10,537,478 B2
APPLICATION NO. : 15/539855
DATED : January 21, 2020
INVENTOR(S) : David Holm Page 1 of 1

It is certified that error appears in the above-identified patent and that said Letters Patent is hereby corrected as shown below:

In the Specification

Column 9
Line 26    Delete "idodophors," and insert -- iodophors, --, therefor.
Line 54    Delete "hydocolloid" and insert -- hydrocolloid --, therefor.
Line 57    Delete "polyisprene" and insert -- polyisoprene --, therefor.

In the Claims

Column 20
Line 56    In Claim 5, delete "1:" and insert -- 1, --, therefor.
Line 62    In Claim 6, delete "1:" and insert -- 1, --, therefor.

Column 21
Line 17    In Claim 11, after "is greater than adhesion to steel" delete "is greater than adhesion to steel".

Column 22
Line 10    In Claim 16, after "between" delete "about".
Line 11    In Claim 16, after "and" delete "about".
Line 16 (Approx.)    In Claim 18, after "porous" delete "absorbent".
Line 20 (Approx.)    In Claim 19, delete "of," and insert -- of claim 1, --, therefor.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*